Figure 1:
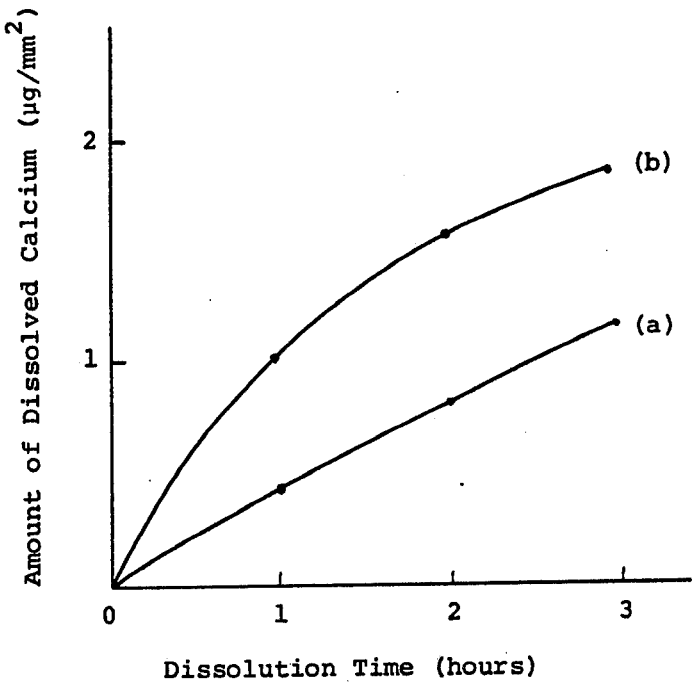

United States Patent [19]

Yamaga et al.

[11] 4,146,606

[45] Mar. 27, 1979

[54] PHARMACEUTICAL COMPOSITIONS FOR DENTAL USE

[75] Inventors: Reiichi Yamaga, No. 1-14-5 Yanagawa-cho, Takatsuki-shi, Osaka-fu; Ichiro Yokomizo, No. 45 Shichikukamihonmachi, Kita-ku, Kyoto-shi, Kyoto-fu; Setsuo Higashi, Tokorozawa, all of Japan

[73] Assignees: Reiichi Yamaga; Ichiro Yokomizo, both of Japan

[21] Appl. No.: 909,871

[22] Filed: May 26, 1978

[30] Foreign Application Priority Data

May 27, 1977 [JP] Japan ................................ 52-62391

[51] Int. Cl.² .......................... A61K 7/16; A61K 7/18; A61K 7/26
[52] U.S. Cl. ........................ 424/52; 424/49; 424/58
[58] Field of Search ........................ 424/48–58

[56] References Cited

U.S. PATENT DOCUMENTS

| | | | |
|---|---|---|---|
| 3,122,483 | 2/1964 | Rosenthal | 424/49 X |
| 3,122,483 | 2/1964 | Rosenthal | 424/49 X |
| 3,699,221 | 10/1972 | Schole et al. | 424/49 X |
| 3,699,221 | 10/1972 | Schole et al. | 424/49 X |
| 3,888,976 | 6/1975 | Mlkvy et al. | 424/49 X |
| 3,888,976 | 6/1975 | Mlkvy et al. | 424/49 X |
| 3,988,434 | 10/1976 | Schole et al. | 424/49 X |
| 3,988,434 | 10/1976 | Schole et al. | 424/49 X |
| 4,022,880 | 5/1977 | Vinson et al. | 424/49 X |
| 4,022,880 | 5/1977 | Vinson et al. | 424/49 X |
| 4,082,841 | 4/1978 | Pader | 424/49 X |
| 4,082,841 | 4/1978 | Pader | 424/49 X |

FOREIGN PATENT DOCUMENTS

| | | |
|---|---|---|
| 959764 | 12/1974 | Canada. |
| 7100701 | 8/1972 | South Africa. |
| 1290627 | 9/1972 | United Kingdom. |
| 1296952 | 11/1972 | United Kingdom. |
| 1373001 | 11/1974 | United Kingdom. |
| 1373003 | 11/1974 | United Kingdom. |

*Primary Examiner*—Shep K. Rose
*Attorney, Agent, or Firm*—Jones, Tullar & Cooper

[57] ABSTRACT

A pharmaceutical composition for dental use which comprises a strontium compound, a zinc compound, tannin and, optionally, a fluorine compound in such a weight proportion that strontium, zinc, tannin and fluorine is 1 to 3:2 to 4:1 to 3:0 to 4.

6 Claims, 2 Drawing Figures

PHARMACEUTICAL COMPOSITIONS FOR DENTAL USE

The present invention relates to a pharmaceutical composition for dental use. More particularly, it relates to a composition useful for treatment of teeth, especially as a protective agent for dentin or an obturating agent for dentinal tubules.

In recent years, remarkable developments are recognized in medical and pharmaceutical sciences, and therapeutic methods for various diseases, which had been considered to be incurable, have been established. However, there are still some diseases, for which no effective therapeutic method has been yet developed. One of such incurable diseases is dental caries.

Teeth are the and sole organs which accomplishes mechanical work in digesting food materials. In spite of the fact that a tooth cannot be recovered after it was once damaged, a satisfactory method for prevention of dental caries has not been established yet.

Up to this time, a fluorine compound has been the most frequently used material for prevention of dental caries, by incorporating the same into tap water or in the form of concentrated aqueous solution. When a concentrated aqueous solution of a fluorine compound is applied to teeth, it induces the decomposition of hydroxyapatite $(Ca_{10}(PO_4)_6(OH)_2)$, which is a principal component of both dental enamel and dentin, and brings about the release of phosphate ion which is an important component of the teeth. Further, since it takes a long time until fluoride ion is combined with phosphate ion and calcium ion and fixed in the form of fluoroapatite $(Ca_{10}(PO_4)_6F_2)$ so as to exert its effect, only a small proportion (at the most 1% by weight) of fluorine ion present in the applied fluoride solution can be effectively utilized so that the therapeutic effect is low.

As the result of an extensive study seeking a new pharmaceutical composition effective in prevention of dental caries, it has now been found that a composition comprising strontium, zinc and tannin, optionally with a fluorine compound possesses both a protective action for dentin and an obturating action for dentinal tubules and is effective not only for prevention of dental caries but also for protection of dental pulp as well as for alleviation of hyperesthesia. This invention is based on the above finding.

According to the present invention, there is provided a pharmaceutical composition for dental use which comprises a strontium compound, a zinc compound, tannin and, optionally, a fluorine compound in such a weight proportion that strontium, zinc, tannin and fluorine is 1 to 3:2 to 4:1 to 3:0 to 4 (particularly 2 to 4).

It is generally recognized that the tooth is constituted of inorganic substances, which mainly comprise hydroxyapatite, dental enamel and dentin, and organic substances which mainly comprise proteins. Both strontium and fluorine in the composition of the invention play a role in strengthening the hydroxyapatite physicochemically, and both zinc and tannin play a role to in coagulating and astringing the proteins so that the invasion of bacteria is inhibited and the dentinal tubules is obturated. More specifically, strontium compensates for the lack of calcium in hydroxyapatite, which is the main component of dental enamel and dentin, and increases the chemical stability of the apatite. Fluorine takes the place of the hydroxyl group in the hydroxyapatite and thus improves the acid proofing property resistance thereof. Zinc and tannin combine respectively with an acid group (e.g. carboxy) and an alkaline group (e.g. amino, imino) in collagen which forms a major component of the proteins and thus coagulate and astringe the proteins.

In preparing of the composition of the invention, a strontium compound, a zinc compound, tannin and, when used, a fluorine compound are mixed together in any order so as to make a composition containing a weight proportion of Sr:Zn:tannin:F of 1 to 3:2 to 4:1 to 3:0 to 4 (particularly 2 to 4). The aforementioned weight proportion has been determined on the basis of the animal and clinical tests and indicates a practically effective range.

Of the components employed in the composition of the invention, fluorine has a relatively high toxicity. Therefore, the composition including fluorine should be used under the strict direction of a dentist. Thus, the composition of the invention containing fluorine is recommended for use by a dentist, while the one not containing fluorine is recommended for household use.

As the fluorine compound, there can be used any water-soluble or insoluble fluoride, and a suitable fluoride may be chosen depending on the use. When, for instance, the composition is used for rinsing the mouth, a water-soluble fluoride is preferably employed. When the composition is desired to be long-acting, a water-insoluble fluoride is favorably employed. Specific examples of the fluorides are sodium fluoride, potassium fluoride, ammonium fluoride, tin fluoride, strontium fluoride, calcium fluoride, etc.

With regard to the strontium compound, it can be water-soluble or water-insoluble depending upon the application of the composition. Examples of the strontium compound include strontium hydroxide, strontium fluoride, strontium chloride, strontium acetate, strontium lactate, etc.

As the zinc compound, the use of a water-soluble compound is preferred. Examples of such compound are zinc fluoride (hydrate), zinc chloride, zinc acetate, acid zinc phosphate, etc.

As the tannin, any of those which are commercially available under the trade name of "tannin" or "tannic acid" can be used.

It should be understood that each of above components, except tannin, is not necessarily required to be in an independent form but may be in a combined form with any other component. Strontium fluoride, for example, may be used as the fluorine compound and also as the strontium compound. Similarly, zinc fluoride is served not only as the fluorine compound but also as the zinc compound. The weight proportion of the components as aforementioned can be applied to these cases.

In general, the composition according to the invention is advantageously provided in the form of a solid preparation. Since all of the components mentioned above are generally in solid states, the mixing of those components gives a powdered preparation. The powdered preparation thus obtained can be applied to a diseased part in the form of a powder. However, it may be used after dispersed in a proper quantity of water. In particular, when the composition is to be used as a mouth rinsing agent, it is advantageous that the composition be in the form of a tablet which is dispersible in water on the use. Further, it is possible that the powder preparation is mixed into a dental cement composition in a weight ratio of 5 to 20:100 and employed in the form of a cement possessing a therapeutic effect. It is also possible to suspend the powder preparation in a non-aqueous viscous solvent, such as glycerol, and then to apply to a diseased part in a paste form.

As understood from the above, the composition of the invention comprises active components which exert an effect, as a whole, to both inorganic and organic parts in teeth. Such a pharmaceutical composition acting on both the organic and inorganic parts of a tooth has not been previously known in the dental field. Further, the composition is generally provided in the form of a solid preparation and can be used either as such, or after being dispersed in a proper medium such as water. Therefore, it is free from disadvantages such as insufficient storage stability and a lack of durable effect as observed in conventional compositions which is principally provided in the form of aqueous solutions.

The solid preparations containing fluorine are very suitable for the treatment of dental caries by a dentist since they, as stated above, can be admixed with a dental cement or a non-aqueous viscous solvent and the mixture thus obtained can be applied to a diseased part, whereby a long acting effect can be expected. This long acting effect can not be achieved by any of conventional preparations of an aqueous solution type.

As have been mentioned above, tannin and zinc contained in the composition according to the invention serve to strengthen the teeth. However, they, when penetrated into the dentin, combine together gradually, as the time passes, to form a precipitate which is also useful for obturating the dentinal tubules.

When the reaction product between tannin and zinc is employed, there is expected neither an individual action of each component nor the effect of the reaction product, because such reaction product itself can not penetrate into the teeth. Therefore, it is also significant in this respect that the composition according to the invention is provided in a solid form.

The invention will now be explained in more detail by the following examples, wherein parts and percentages are by weight unless otherwise indicated.

EXAMPLE 1

The following components, each in the form of powder, were mixed uniformly to give a powdered preparation for use by a dentist:

| Component | Part(s) |
| --- | --- |
| $SrF_2$ | 3 |
| $ZnF_2$ | 4 |
| tannin | 2 |
| pH regulating agent (zinc oxide) | slight amount |

EXAMPLE 2

The following components, each in the form of powder, were mixed uniformly to give a powdered preparation for household use:

| Component | Part(s) |
| --- | --- |
| $Sr(OCOCH_3)_2$ | 3 |
| $Zn(OCOCH_3)_2$ | 3 |
| tannin | 2 |

EXAMPLE 3

A tablet (1 g/Tab) was produced by a conventional method using the components below:

| Component | Part(s) |
| --- | --- |
| $Sr(OCOCH_3)_2$ | 3 |
| $Zn(OCOCH_3)_2$ | 3 |
| tannin | 2 |
| caking agent | slight amount |

REFERENCE EXAMPLE 1

Two abuttal teeth were prepared for crown attachment in one and the same patient. The dentin surface of one of the abuttal teeth was covered with 0.05 g of the powdered preparation according to Example 1 and subjected to transitory sealing, whereas the other tooth was temporarily sealed without applying the powdered preparation. After 10 days or more, abrasion pain was tested with the aid of a exploring-needle prior to the crown attachment.

The results are shown in Table 1.

Table 1

| Pain degree | Number of teeth | |
| --- | --- | --- |
|  | Powdered preparation used | Powdered preparation not used |
| Severe | 0 | 1 |
| Weak | 4 | 8 |
| Slight | 5 | 10 |
| None | 12 | 2 |

From Table 1, it is clear that desensitization of the dentin occurs when the powdered preparation of the invention is used.

REFERENCE EXAMPLE 2

As the first step, the electric resistance ($R_1$) of a dentinal tubules existing between a dental pulp and an acquired cavity was measured after the cavity had been filled with saline. Thereafter, 100 parts by weight of eugenol cement for dental use which had been chosen as cement for temporary sealing was mixed with 20 parts by weight of the powdered preparation according to Example 1 and the resultant mixture was filled in the cavity.

After about one week, the mixed cement, which had been used for temporary sealing, was removed and amalgam was packed into the cavity, and the electric resistance ($R_2$) was measured again. The greater the resistance ratio ($R_2/R_1$) is, the more effectively a dentinal tubule is obturated with good interception of outer stimulus. The test results are shown in Table 2 together with comparisons in which no powdered preparation of the invention was applied.

Table 2

| Case | Resistance ratio of dentinal tubules ($R_2/R_1$) | |
| --- | --- | --- |
|  | Powdered preparation used | Powdered preparation not used |
| 1 | 1.6 | 1.1 |
| 2 | 1.4 | 1.0 |
| 3 | 1.4 | 1.0 |
| 4 | 1.3 | 1.2 |
| 5 | 1.5 | 1.2 |
| 6 | 1.6 | 1.3 |
| 7 | 1.5 | 1.0 |
| 8 | 1.5 | 1.1 |
| 9 | 1.7 | 1.0 |
| 10 | 1.6 | 1.1 |

Table 2-continued

| | Resistance ratio of dentinal tubules ($R_2/R_1$) | |
|---|---|---|
| Case | Powdered preparation used | Powdered preparation not used |
| Average | 1.5 | 1.1 |

Table 2 clearly shows that the obturation of dentinal tubules, desensitization and the protection of dental pulp are achieved by the use of the powdered preparation.

REFERENCE EXAMPLE 3

The therapeutic effect of the composition (powdered preparation) of the invention according to Example 1 on hyperesthesia of the neck of the tooth was tested. For this purpose, according to the method of Aono et al. (The Japanese Journal of Conservative Dentistry, Vol. 10, page 31, 1967), 20 parts by weight of the powdered preparation of Example 1 and 100 parts by weight of powdered eugenol cement for dental use were mixed and kneaded, the kneaded mixture being subsequently adhered to the tooth of a patient who felt severe pain in the tooth neck. For the purpose of comparison, eugenol cement free from the powdered preparation was adhered to another tooth of a patient, who felt severe pain in the tooth neck, and one week later then, thermo-pain and abrasion pain on the teeth as treated above were tested. The results are shown in Table 3.

Table 3

| | Thermo-pain (with water of 15° C) | | Abrasion pain (with a metal plate) | |
|---|---|---|---|---|
| Pain degree | Powdered preparation used (Number of tooth) | Powdered preparation not used (Number of tooth) | Powdered preparation used (Number of tooth) | Powdered preparation not used (Number of tooth) |
| Severe | 0 | 2 | 0 | 3 |
| Weak | 0 | 6 | 0 | 5 |
| Slight | 3 | 2 | 4 | 2 |
| None | 7 | 0 | 6 | 0 |

From Table 3, it is clear that the use of the powdered preparation of Example 1 exhibits desensitization effect on the neck of the tooth.

REFERENCE EXAMPLE 4

The dental enamel of an extracted tooth was immersed all day long in the suspension which had been prepared by dispersing 2 g of the powdered preparation according to Example 2 into 10 ml of water. The surface of the extracted tooth thus treated was coated with paraffin and, thereafter, an window of 3 mm in diameter was opened in the paraffin layer so formed. The paraffin-coated tooth were subsequently immersed in an acetic acid buffer solution of pH 4.6 for one, two and three hours, respectively, whereupon the quantity of dissolved calcium was measured in each case. The similar measurement was performed on the extracted tooth analogously treated as above, but not immersed in the suspension of the powdered preparation.

The results are shown in FIG. 1, wherein the axis of abscissa and the axis of ordinates indicate respectively a dissolution time (hour) and an amount of dissolved calcium ($\mu g/mm^2$), and curves (a) and (b) show the respective cases in which the dental enamel was treated and not treated with the powdered preparation.

From the comparison of the curves (a) and (b), it is well understood that the treatment with the powdered preparation increases an anti-acid property of dental enamel and that it is useful for the prevention of a dental caries.

REFERENCE EXAMPLE 5

The mouth of a patient who suffers from hyperesthesia on the neck of the tooth was rinsed for 30 minutes, three times a day, using the suspension which had been prepared by dispersing 2 g of the powdered preparation according to Example 2 into 10 ml of water. An abrasion pain was measured every four days after the above treatment. The results are shown in Table 4.

Table 4

| | Desensitization effect (Number of teeth) | | | | | |
|---|---|---|---|---|---|---|
| Pain degree | days 0 | 4 | 8 | 12 | 16 | 20 |
| Severe | 20 | 17 | 11 | 6 | 3 | 1 |
| Weak | 0 | 3 | 8 | 6 | 4 | 4 |
| Slight | 0 | 0 | 1 | 5 | 3 | 2 |
| None | 0 | 0 | 0 | 3 | 10 | 13 |

From Table 4, it is clear that desensitization is enhanced with a prolonged period of time during which the mouth rinsing by the use of the aqueous solution of the powdered preparation of the invention is performed.

REFERENCE EXAMPLE 6

Figure 2:
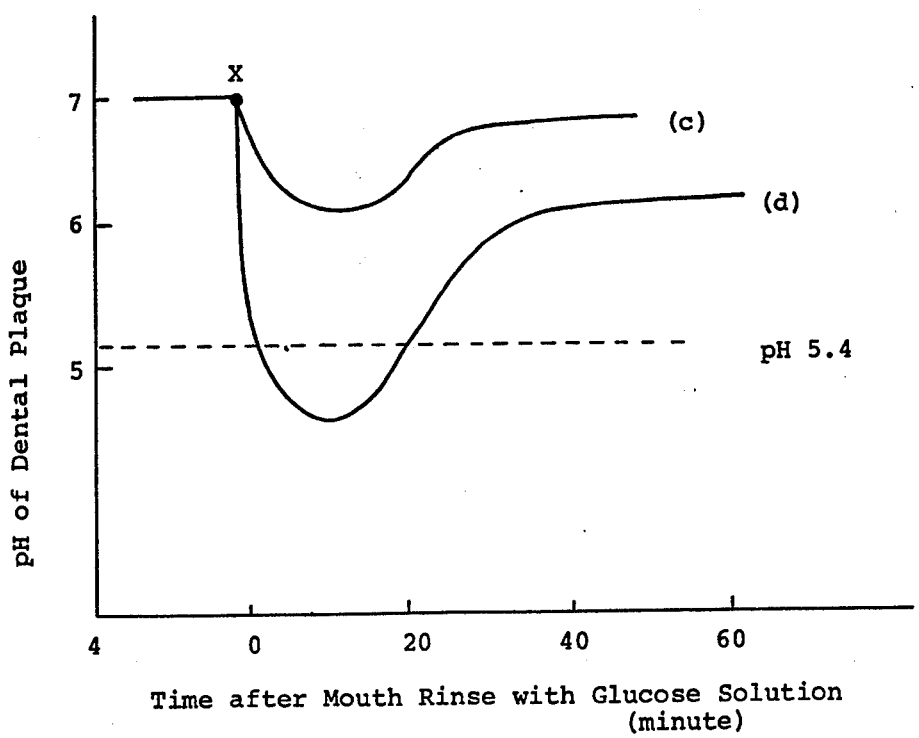

According to Stephan's method (Pedodontia; translated by Othiai, page 225, issued by Ishiyaku Schuppan, 1969), variation in pH of dental plaque was measured when a mouth rinse was performed between meals using an aqueous solution of glucose. The results are shown in FIG. 2, wherein the axis of abscissa and the axis of ordinates represent respectively the lapse of time (minutes) after the mouth rinse and pH of dental plaque. In FIG. 2, a curve (c) shows variation in average pH of dental plaque in five patients who performed the mouth rinse twice a day after meal in such a manner as to crunch two tablets according to Example 3 and then wash the mouth with 10 ml of water, and a curve (d) shows variation in average pH of dental plaque in five patients who did not perform the mouth rinse. A character X indicates the time of mouth rinse with glucose.

Comparing the curves (c) and (d), it will be understood that, by the use of the tablet according to the invention in the mouth rinse, the pH of dental plaque never falls below 5.4, which is the value of the critical acidity for making a tooth dissolved, and that the outbreak of a dental caries could be suppressed in spite of the presence of dental plaque.

What is claimed is:

1. A pharmaceutical composition for dental use which comprises a strontium compound, a zinc compound and tannin in such a weight proportion that strontium, zinc and tannin is 1 to 3:2 to 4:1 to 3.

2. The composition according to claim 1 which further comprises a fluorine compound.

3. The composition according to claim 2 wherein the weight proportion of strontium, zinc, tannin and fluorine is 1 to 3:2 to 4:1 to 3:0 to 4.

4. The composition according to claim 1 which is in a solid preparation form.

5. A method for preventing dental caries which comprises applying the composition according to claim 1 to a tooth.

6. A method for preventing the progress of dental caries which comprises applying the composition according to claim 1 to a tooth in a decayed state.

* * * * *